(12) United States Patent
Henderson et al.

(10) Patent No.: US 7,147,617 B2
(45) Date of Patent: Dec. 12, 2006

(54) ARTERIO-VENOUS SHUNT GRAFT

(75) Inventors: Jamie S. Henderson, Oakland, NJ (US); Warren A. Joeckel, Wayne, NJ (US); Ronald Rakos, Neshanic Station, NJ (US)

(73) Assignee: Scimed Life Systems, Inc., Maple Grove, MN (US)

( * ) Notice: Subject to any disclaimer, the term of this patent is extended or adjusted under 35 U.S.C. 154(b) by 275 days.

(21) Appl. No.: 09/994,551

(22) Filed: Nov. 27, 2001

(65) Prior Publication Data

US 2003/0100859 A1  May 29, 2003

(51) Int. Cl.
*A61M 5/00* (2006.01)
*A61M 5/37* (2006.01)
*A61B 17/05* (2006.01)

(52) U.S. Cl. .................. 604/8; 604/6.16; 604/264; 606/153

(58) Field of Classification Search ............... 604/8–9, 604/6.16, 7, 264, 523–524, 532, 171, 174–5, 604/96.01, 104–109, 164.01–164.04, 164.08, 604/165.01–165, 175; 623/1.1, 1.24, 1.32, 623/11.11, 23.64, 23.68, 23.7, 23.71, 1.12, 623/1.2, 1.21, 1.23, 1.28–1.29, 23.67, 23.74; 606/108, 153, 191, 194, 198; 428/34.1, 34.3, 428/36.5, 36.9
See application file for complete search history.

(56) References Cited

U.S. PATENT DOCUMENTS

| | | | | |
|---|---|---|---|---|
| 4,969,896 A | * | 11/1990 | Shors ........................ 623/1.44 |
| 5,129,910 A | * | 7/1992 | Phan et al. ................ 606/127 |
| 5,556,426 A | * | 9/1996 | Popadiuk et al. .......... 623/1.33 |
| 5,609,624 A | * | 3/1997 | Kalis ........................ 623/1.32 |
| 5,866,217 A | * | 2/1999 | Stenoien et al. ........... 623/1.44 |
| 5,984,965 A | * | 11/1999 | Knapp et al. .............. 623/23.7 |
| 5,993,483 A | * | 11/1999 | Gianotti .................... 623/1.22 |
| 6,280,423 B1 | * | 8/2001 | Davey et al. ............... 604/264 |
| 6,319,279 B1 | | 11/2001 | Kuo et al. |
| 6,416,537 B1 | * | 7/2002 | Martakos et al. .......... 623/1.13 |
| 6,926,735 B1 | * | 8/2005 | Henderson ................ 623/1.42 |

OTHER PUBLICATIONS

Search Report issued on Mar. 26, 2003 for International Application No. PCT/US 02/29292 filed Sep. 16, 2002.

* cited by examiner

*Primary Examiner*—Patricia Bianco
(74) *Attorney, Agent, or Firm*—Hoffmann & Baron, LLP

(57) ABSTRACT

A graft, for example, an arterio-venous shunt graft, is provided, which in a first aspect of the subject invention, is formed with longitudinal ribs. With fibrotic tissue ingrowth between the ribs, a composite rib/tissue layer is formed about the graft. The ribs provide counteracting lateral force against the embedded tissue to seal punctures formed therethrough during hemodialysis procedures. To provide additional surface area for puncturing, the graft may be formed with a truncated cross-section. With a second aspect of the invention, the graft is mounted onto a strip to prevent kinking, twisting or bending during an implantation procedure.

20 Claims, 8 Drawing Sheets

ARTERIO-VENOUS SHUNT GRAFT

FIELD OF THE INVENTION

This invention relates to implantable prostheses, and, more particularly, to arterio-venous (AV) shunt grafts for hemodialysis applications.

BACKGROUND OF THE INVENTION

Patients suffering from renal failure who undergo hemodialysis treatment require their blood to be readily accessible for such treatment. To avoid repeated puncturing of blood vessels, a technique has been developed in the prior art, wherein a graft is implanted that acts as a shunt between an artery and a vein, such graft being aptly referred to as an arterio-venous (AV) shunt graft. Typically, the AV graft is of relatively long length to provide maximum length for needle puncturing. Because of the relatively long length, the AV graft typically has a longer length than the spacing between the relevant artery and vein, and, as such, is often bent into a U-shape. For implantation, two relatively shallow channels are subcutaneously "tunneled" into the necessary U-shaped pattern, with a tunneller or guidewire being used to draw the AV graft into proper position. The ends of the graft are sutured, or are otherwise connected to, the selected artery and vein.

To limit the amount of blood diverted through the AV graft, and away from artery, the AV graft may have a tapered end at its arterial connection. In this manner, blood flow through the AV graft is restricted, without sacrificing surface area for needle puncture sites.

Although conventional AV grafts may provide relief for the vasculature, sealing of puncture sites therein is of major concern because of blood loss, as well as concern for the overall structural integrity of the graft. One approach to this problem has been in delaying a minimum number of days, often as long as two weeks or more, after implantation before puncturing the AV graft. The minimum delay period allows fibrotic tissue to surround the graft. Thus, upon puncturing, the body is naturally able to cause a clot and restrict blood loss.

A second and different approach has been the use of self-sealing grafts, which typically rely on fibrous material or sealant material to seal over a puncture. Examples of this approach are found in U.S. Pat. No. 4,619,641 to Schanzer; U.S. Pat. No. 5,192,310 to Herweck et al.; and U.S. Pat. No. 5,700,287 to Myers et al. Because of the additional self-sealing material applied to this set of grafts, these AV grafts often have relatively large diameters.

Due to the repeated puncturing of AV grafts, AV grafts have a limited life, regardless of design. Whereupon the structural integrity and/or the sealing ability of the AV graft becomes excessively compromised, a new AV graft is implanted into the patient at a new location. Patients who require hemodialysis over extensive periods of time may have multiple AV grafts implanted in them. As is readily apparent, it is desired to provide an AV graft having an extended life, to minimize the need for additional AV graft implantations in a patient.

SUMMARY OF THE INVENTION

In a first aspect of the subject invention, an AV shunt graft is provided having longitudinal ribs formed on at least a portion of an outer surface thereof. The ribs act to encourage fibrotic tissue ingrowth, resulting in a composite tissue/rib layer being formed about the AV graft. The ribs apply a counteracting lateral force against any displaced embedded fibrotic tissue disposed between the ribs (when there is a puncturing of the tissue), thereby aiding in the sealing thereof.

In a preferred embodiment, the AV graft is also at least partially truncated, having a generally D-shaped cross-section with the ribs being located on an arcuate portion thereof. Upon implantation, the AV graft is positioned so that the arcuate portion faces the skin of the patient. Accordingly, maximum surface area is provided for needle puncturing. In comparing the subject invention with a conventional AV graft, the profile length of the arcuate portion of the subject invention is formed longer than half the circumference of a conventional circular graft, to provide increased area for needle puncturing, while the cross-sectional area of the subject invention is at least equivalent to that of the conventional device so that sufficient flow area is maintained.

In a second aspect of the invention, the AV graft is mounted onto, preferably by sintering, a flat strip prior to implantation. As such, the AV graft may be permanently pre-formed into a desired shape for implantation (typically a U-shape), without concern for kinking, twisting, or bending, which are problems commonly experienced with implantation of prior art AV grafts. In addition, the mounted AV graft is implantable as an integral unit, which requires a single tunnel to be formed, rather than two tunnels, as with conventional devices.

As a variation of the second aspect of the invention, a second strip may be mounted onto the top of the AV graft, to provide additional rigidity and to enhance self-sealing characteristics. A layer of sealant material may be disposed adjacent to the first and/or second strip.

These and other features of the invention will be better understood through a study of the following detailed description and accompanying drawings.

DETAILED DESCRIPTION OF THE INVENTION

Figure 1:
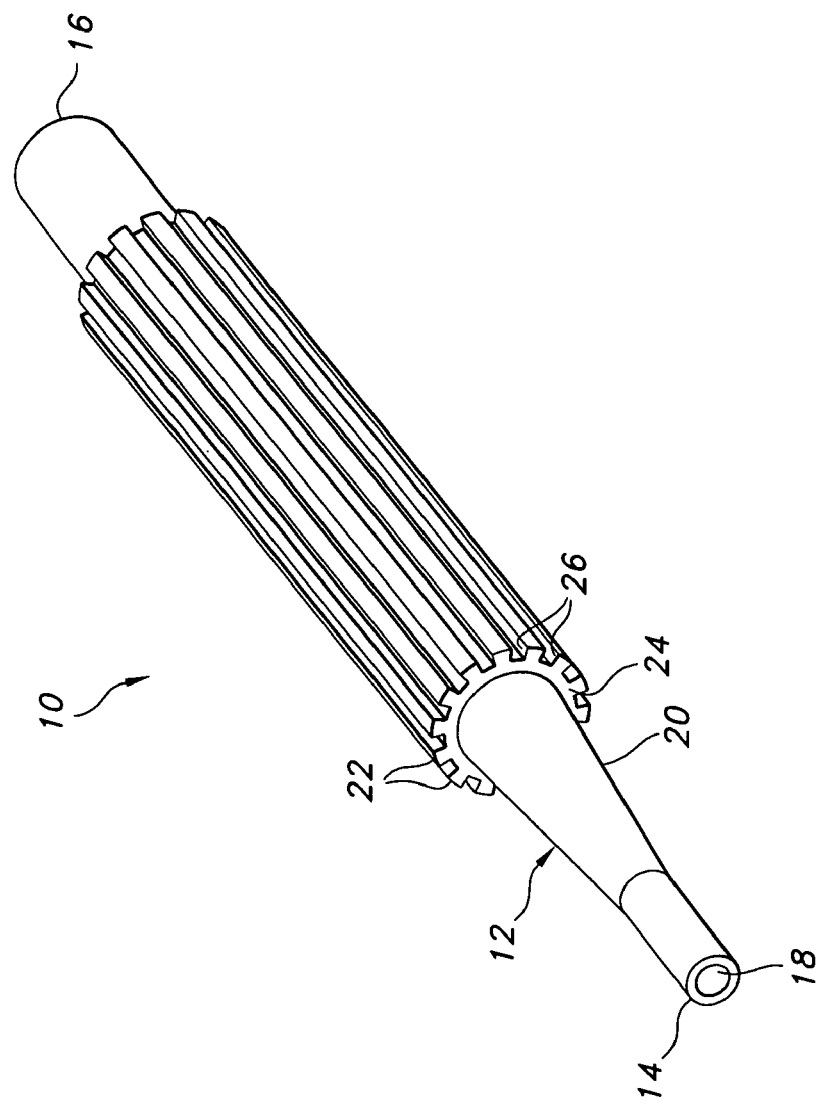
FIG. 1 is a perspective view of an arterio-venous (AV) shunt graft formed in accordance with a first aspect of the subject invention.
Figure 2:
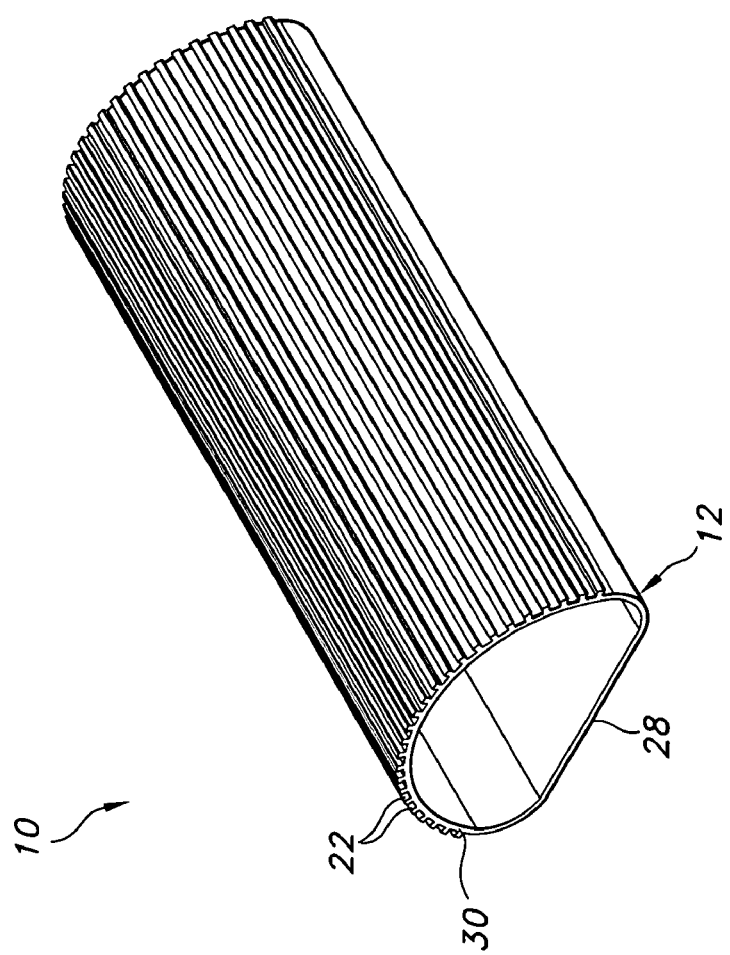
FIG. 2 is a cross-sectional perspective view of a graft having a truncated cross-section.

With reference to FIGS. 1 and 2, in a first aspect of the subject invention, a graft is provided having longitudinal ribs extending therefrom. It is envisioned that the use of ribs is particularly well-suited for arterio-venous (AV) shunt grafts ("AV grafts"), although it may be used with other types of grafts, including endovascular grafts. To illustrate the subject invention, reference will be made to AV grafts, although the ribs may be formed on other types of grafts.

Referring to FIG. 1, an AV graft 10 is shown, having a main body 12 with an arterial end 14, a venous end 16, and a lumen 18 extending therebetween. The main body 12 may have a tapered portion 20 in proximity to the arterial end 14, so as to reduce the cross-sectional area of the lumen 18 at the arterial end 14. As such, the amount of blood flow that is divertable through the AV graft 10 is limited. The main body 12 may be formed of any material known to those skilled in the art used to form vascular prostheses, such as a textile material (e.g., polyethylene terephthalate (PET)), a polymeric material (e.g., expanded polytetrafluoroethylene (ePTFE)), or a composite thereof.

A plurality of ribs 22 are formed to extend from the main body 12. In a preferred embodiment, the ribs 22 are unitarily formed on a sleeve 24, with the rib 22/sleeve 24 structure being separately extruded from the main body 12. With this preferred arrangement, the main body 12 may be formed separately in accordance with similar techniques for manufacturing conventional AV grafts. The sleeve 24 desirably has an internal diameter or lumen opening which is larger than the external diameter or dimension of main body 12 so that the sleeve 24 may be slipped over the main body 12 during assembly (e.g., with the main body 12 being mounted on a mandrel), and caused to shrink thereonto. In such cases, the sleeve 24 may be joined or immovably fixed to the main body 12 using a variety of techniques including adhesive bonding, solvent bonding, hot melt bonding or sintering. Sintering is particularly desirable. It is also desired to have the internal lumen of the sleeve 24 be smooth.

When sintering the sleeve 24 to the main body 12, heat is employed. Optionally, pressure may also be employed. It is desirable that the materials used to form the respective components have a softening or sintering temperature which permits their bonding without damage to their structural integrity. In one particularly desirable aspect of the invention, the body 12 and the ribs 22/sleeve 24 structures are made of the same material, such as ePTFE.

As an alternative, the main body 12 may be extruded with the ribs 22. If so, the ribs 22 would extend the full longitudinal length of the AV graft 10, which may not be desired in all cases.

Each of the ribs 22 is preferably formed generally straight to extend longitudinally along at least a portion of the AV graft 10. It is preferred that the ribs 22 be coextensive with a major portion of the main body 12, yet be spaced from the arterial and venous ends 14 and 16, to allow for proper suturing or attachment thereof to the native vessels. In addition, the ribs 22 are circumferentially spaced-apart about the AV graft 10, and, preferably, are evenly-spaced. Because of the circumferential spacing, channels 26 are defined between the ribs 22 into which fibrotic tissue may grow. With tissue ingrowth, a composite rib 22/tissue layer may be formed about the AV graft 10. In addition, it is preferred that the ribs 22 be formed of a material having biocompatibility, such as PTFE (particularly ePTFE). The ribs 22 react to a puncture of the AV graft 10 by applying a counteracting lateral force against any displaced embedded fibrotic tissue to limit blood loss, and aiding in sealing any such punctures.

Figure 3:
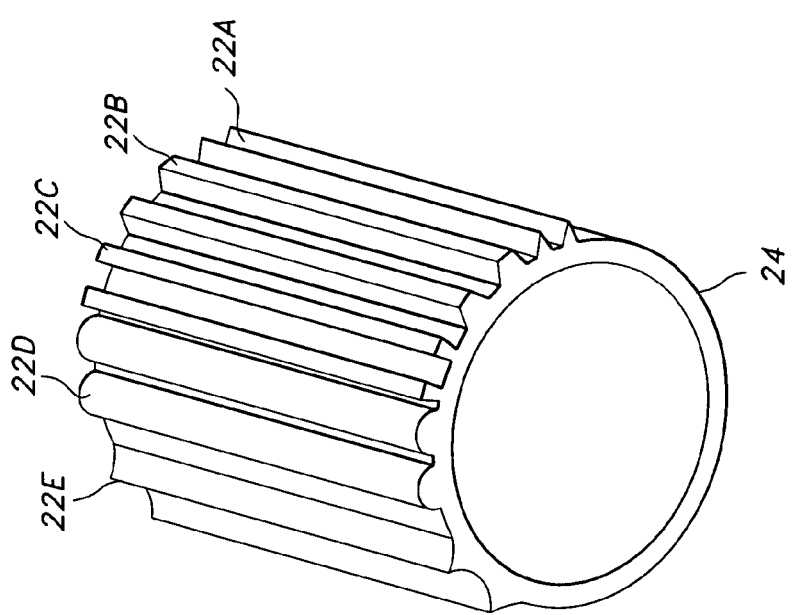
FIG. 3 is a cross-sectional perspective view depicting various rib cross-sectional shapes usable with the subject invention.
Figure 4:
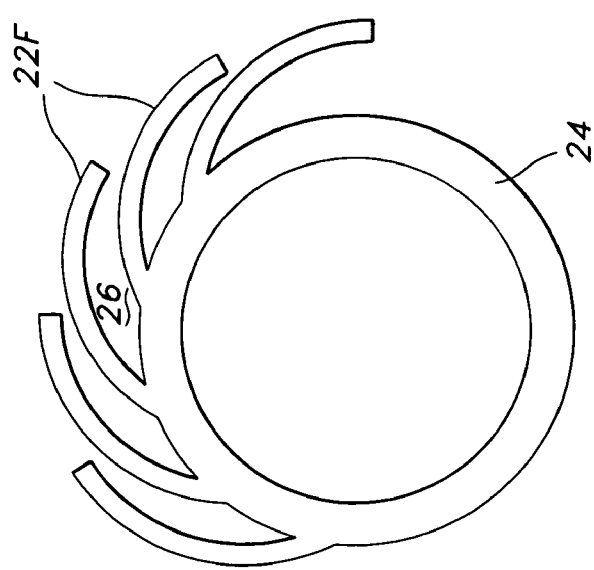
FIG. 4 is a cross-sectional view showing an arrangement of overlapping ribs.

To enhance fibrotic tissue ingrowth, with reference to FIG. 3, the ribs 22 may be formed with various cross-sectional shapes, such as, but not limited to, rib 22A having a triangular cross-section; rib 22B having a trapezoidal cross-section; rib 22C having a dove-tail cross-section; rib 22D having a semi-circular cross-section; and, rib 22E having a pointed cross-sectional shape. Although not shown, other shapes are possible, such as a rectangular cross-section. Alternatively, as shown in FIG. 4, the ribs 22 may be formed to overlap, such as overlapping ribs 22F, wherein the ribs 22F overlap portions of adjacent channels 26. The overlapping ribs 22F not only encourage tissue ingrowth, but act as flap valves in overlying any punctured, embedded fibrotic tissue. Furthermore, the surfaces of the ribs 22, as well as the channels 26, may be textured and/or treated with an ingrowth-enhancing agent. As an alternative, a sealant material may be disposed in the channels 26 to enhance self-sealing characteristics of the AV graft 10. The channels 26 may be filled to varying levels of the sealant, which would also allow for varying degrees of tissue ingrowth.

Figure 2A:
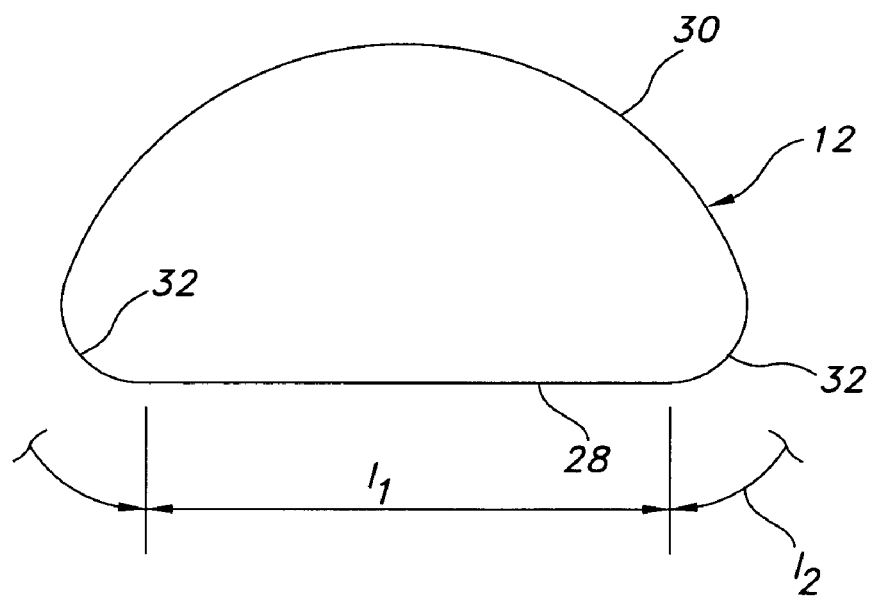
FIG. 2A is a cross-sectional view of a profile of a graft having a truncated cross-section.

In a preferred embodiment, the AV graft 10 is at least partially formed with a truncated cross-section, as shown in FIG. 2. The length of the truncated cross-sectional portion of the AV graft 10 is preferably coextensive with the ribs 22. In a preferred embodiment, the main body 12 includes integrally formed first and second walls 28, 30, with the first and second walls 28, 30 preferably having different profiles. The first wall 28 is preferably formed with a flat profile, whereas the second wall 30 is formed with an arcuate profile, thereby giving the AV graft 10 a generally D-shaped cross-section. It is further preferred that the profile length of the second wall 30 be greater than the profile length of the first wall 28 so that, referring to FIG. 2A, length L2 of the second wall 30 is greater than length L1 of the first wall 28. Upon implanting the AV graft 10, the first wall 28 is positioned to face the patient's skin. By increasing the profile length of the second wall 30, as compared to conventional circular graft designs, additional surface area is provided for puncturing. As shown in FIG. 2A, it is preferred that the second wall 30 be formed with rounded corners 32 in proximity to the first wall 28.

Other truncated cross-sectional shapes than that shown in the Figures may be used. For example, the rounded corners 32 need not be used with a-truncated circle being defined having the first wall 28 follow a chordal path across a circular shape defined by the second wall 30. In addition, the second wall 30 may define an elliptical profile. Furthermore, the first wall 28 may be formed with an arcuate profile (in fact, as a flat profile, the first wall 28 is a curve formed about a radius equal to infinity). In addition, the first and second walls 28, 30 may be formed with the same profile to provide a symmetrical cross-section (e.g., an oval), or different profiles.

To achieve the truncated cross-section, it is preferred that the AV graft 10 be sintered into the desired shape on an appropriately formed mandrel. Specifically, the AV graft 10 is initially oversized and telescoped over the mandrel for sintering. Alternatively, the AV graft 10 may be extruded with the truncated cross-section.

In determining the dimensions of the truncated cross-section, it is desired to at least maintain the same general cross-sectional area available in conventional grafts, thereby ensuring that sufficient flow-through-area of the AV graft 10 is provided.

As noted above with respect to the ribs 22, the truncated cross-sectional shape may be used in conjunction with grafts other than AV grafts.

Figure 5:
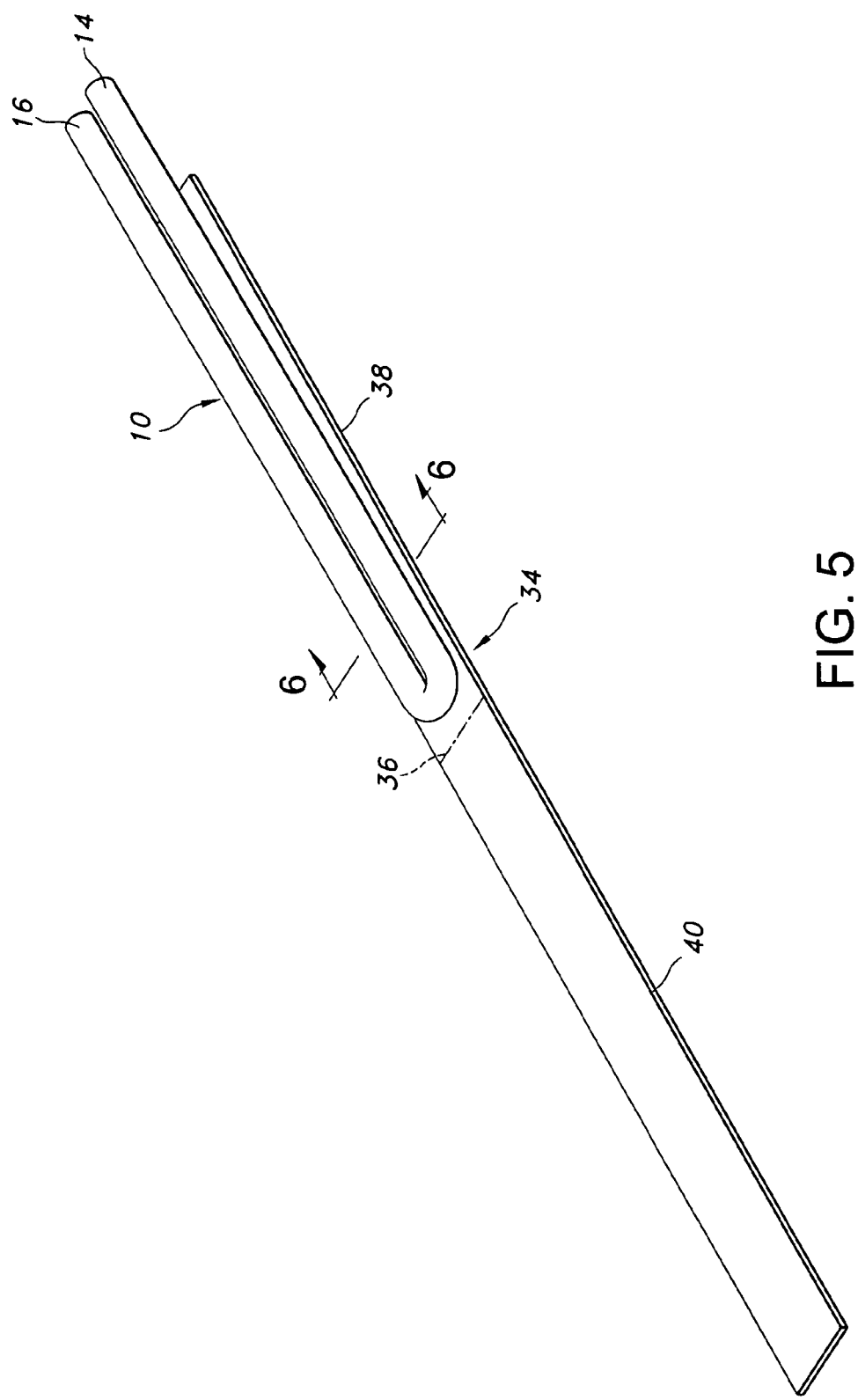
FIG. 5 is a perspective view of a graft mounted onto a strip ready for implantation.

In a second aspect of the subject invention, the AV graft 10 is fixedly mounted onto a strip 34 prior to implantation. The strip 34 is preferably formed of a biocompatible polymeric material, such as ePTFE, with the AV graft 10 being sintered thereto. As shown in FIG. 5, advantageously, the AV graft 10 may be fixedly mounted in a desired shape, and maintained in that shape throughout implantation. It is envisioned that the AV graft 10 will typically be pre-formed in a U-shape.

The strip 34 is optionally formed with a weakened region 36 (e.g., an array of perforations) which allows for an implantable portion 38 of the strip 34 to be separated from a handling portion 40 of the strip 34. The weakened region 36 is located in proximity to the AV graft 10, but preferably does not underlie any portion of the AV graft 10 and, thus, does not affect any of the connection between the AV graft 10 and the strip 34. With the AV graft 10 being mounted onto the strip 34 prior to implantation, kinking, twisting and bending of the AV graft 10 can be avoided during implantation. Furthermore, with the fixed positioning of the AV graft on the strip 34, only a single tunnel need be subcutaneously formed in a recipient. Once implanted, the handling portion 40 of the strip is detached from the implantation portion 38 by causing failure of the weakened region 36, for example, by trimming along the array of perforations. If no weakened region 36 is provided, the handling portion 40 is detached, e.g., by trimming, from the implantation portion.

The implantation portion 38 is preferably formed with a shorter length than the AV graft 10 so as not to be coextensive therewith. Accordingly, the arterial and venous ends 14 and 16 are left free to allow for easy access in suturing or attachment thereof. It should also be noted that the strip 34 need not include the handling portion 40.

Figure 6:
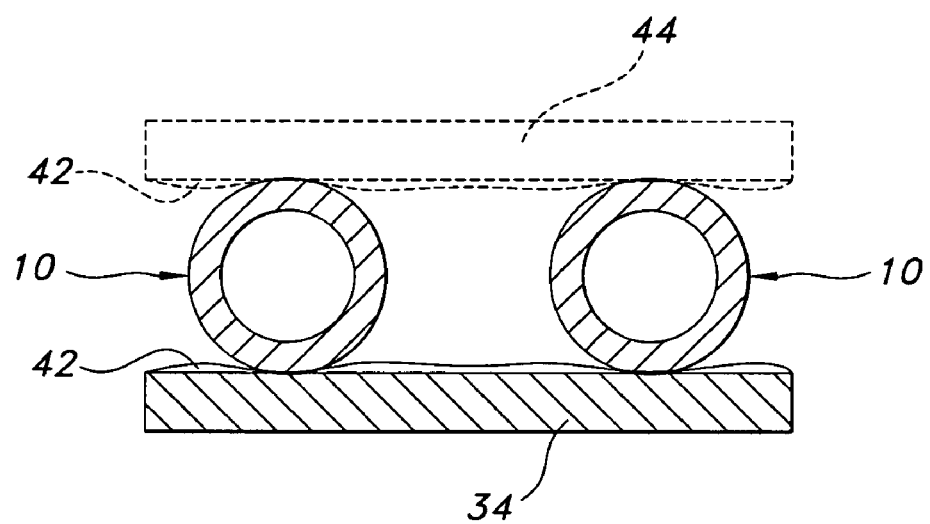
FIG. 6 is a cross-sectional view taken along line 6—6 of FIG. 5.

As a further variation, the AV graft 10 can be mounted onto the strip 34 using an adhesive. Furthermore, as shown in FIG. 6, a self-sealing layer 42 may optionally be disposed between the strip 34 and the AV graft 10, which may be an elastomeric polymer material or a textile have sufficient elastomeric or stretching features. The self-sealing layer 42 serves to react to any punctures formed therethrough to reduce blood loss. As a further variation, a secondary strip 44 may be disposed atop the AV graft 10 so as to "sandwich" the AV graft 10 therebetween, as shown in dashed lines in FIG. 6. The secondary strip 44 would add further rigidity to the assembly in facilitating ease of implantation and additional sealing characteristics against punctures. A self-sealing layer 42 may optionally be disposed between the AV graft 10 and the secondary strip 44.

Figure 7:
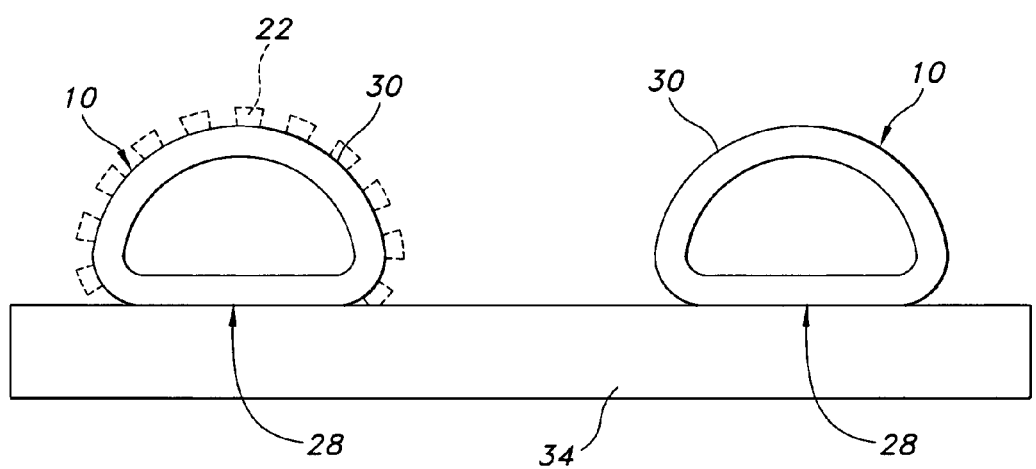
FIG. 7 is a similar view to FIG. 6, wherein the graft is formed with a truncated cross-section.

As a result of utilizing the second aspect of the subject invention, not only will the life of the AV graft 10 be significantly increased, but also, operating time will be reduced and the implantation procedure simplified. Furthermore, the fixed mounting of the AV graft 10 prior to implantation will allow for an optimal bend radius to be pre-selected for flow characteristics in avoiding thrombus formation. It should also be noted that the second aspect of the subject invention may be used in connection with or separate from the first aspect of the subject invention and/or may be used with grafts other than AV grafts, as well as other implantable tubular conduits. As shown in FIG. 7, where the AV graft 10 is formed with at least a partially truncated cross-section (as described above with respect to the first aspect of the invention), it is preferred that the first wall 28, having a shorter profile, be fixedly mounted to the strip 34, with the second wall 30 being free. Upon implantation, the second wall 30 is desirably oriented towards the patient's skin to be punctured and may be optionally formed with the ribs 22 (as shown in dashed lines in FIG. 7).

Various changes and modifications can be made to the present invention. It is intended that all such changes and modifications come within the scope of the invention as set forth in the following claims.

What is claimed is:

1. An arterio-venous shunt graft comprising:
   a tubular body having an interior surface and an exterior surface, a plurality of ribs extending from said exterior surface, said ribs having uncovered portions for direct contact with surrounding body tissue, wherein said tubular body includes a tubular sleeve, said ribs being formed unitarily with, and extending from, said sleeve, wherein said ribs are each generally straight and parallel to a longitudinal axis extending between ends of said tubular body.

2. A graft as in claim 1, wherein said ribs are formed of a biocompatible material.

3. A graft as in claim 2, wherein said material is a polymeric material.

4. A graft as in claim 3, wherein said material is expanded polytetrafluoroethylene.

5. A graft as in claim 1, wherein said ribs extend longitudinally.

6. A graft as in claim 1, wherein said ribs are circumferentially spaced-apart.

7. A graft as in claim 1, wherein said ribs have a trapezoidal cross-section.

8. A graft as in claim 1, wherein said ribs have a triangular cross-section.

9. A graft as in claim 1, wherein said ribs have a semi-circular cross-section.

10. A graft as in claim 1, wherein said ribs have a dove-tail cross-section.

11. A graft as in claim 1, wherein said ribs have a pointed cross-section.

12. A graft as in claim 1, wherein a first of said ribs is circumferentially spaced from a second of said ribs with a channel being defined therebetween, said first rib at least partially overlapping said channel.

13. A graft as in claim 1, wherein a sealant material is disposed adjacent to at least a portion of said ribs.

14. A graft is in claim 1, wherein said ribs are not coextensive with said body.

15. A graft as in claim 1, wherein said tubular body is at least partially defined by first and second integral walls, said first and second walls collectively defining a truncated cross-section.

16. A graft as in claim 15, wherein said cross-section is generally D-shaped.

17. A graft as in claim 15, wherein said first wall has a shorter profile length than said second wall.

18. A graft as in claim 15, wherein said ribs are not coextensive with said truncated cross-section portion of said body.

19. A graft as in claim 1, wherein said tubular body includes first and second ends, said first end having a flow area larger than the flow area of said second end.

20. An arterio-venous shunt graft comprising:
   a tubular body having an arterial end, a venous end with a flow area larger than the flow area of said arterial end, an interior surface and an exterior surface, a plurality of ribs extending from said exterior surface, said ribs having uncovered portions for direct contact with surrounding body tissue, wherein said ribs are each generally straight and parallel to a longitudinal axis of said tubular body extending between said arterial end and said venous end.

* * * * *